United States Patent [19]

Moncla

[11] 4,140,579
[45] Feb. 20, 1979

[54] METHOD OF TESTING FOR PHOSPHOLIPASES USING A COMPOSITION CONTAINING A UNIFORM DISPERSION OF A PHOSPHOLIPID

[76] Inventor: Bernard J. Moncla, 2106 Bermuda St., Long Beach, Calif. 90804

[21] Appl. No.: 784,059

[22] Filed: Apr. 4, 1977

[51] Int. Cl.$^2$ ............................................. G01N 31/14
[52] U.S. Cl. ............................... 195/99; 195/103.5 R; 195/127
[58] Field of Search ................. 195/99, 101, 103.5 R, 195/66 R, 30, 127

[56] References Cited

U.S. PATENT DOCUMENTS

| | | | |
|---|---|---|---|
| 3,894,844 | 7/1975 | Pinto et al. | 23/230 B |
| 3,917,515 | 11/1975 | Goldberg | 195/103.5 R |

OTHER PUBLICATIONS

Dennis, "Formation and Characterization of Mixed Micelles of the Nonionic Surfactant Triton X-100 with Egg, Dipalmitoyl, and Dimyristoyl Phosphatidylcholines", Arch. Biochem. Biophys., vol. 165 (1974), pp. 764-773.
Ikezawa et al., "Studies on Phosphatidylinositol Phosphodiesterase (Phospholipase C Type) of *Bacillus cereus*", Biochim. Biophys., Acta, vol. 450 (1976), pp. 154-164.
Hayakawa et al., "Preparation of Artificial Vesicles Having an L-Alanine Uptake Activity Which Requires NAPH as Energy Source", Biochem. and Biophys. Research Com., vol. 72, No. 4 (1976), pp. 1548-1553.
Cooper et al., "Factors Influencing the Lipid Composition and Fluidity of Red Cell Membranes in Vitro: Production of Red Cells Possessing More Than Two Cholesterols per Phospholipid", Biochemistry, vol. 17 (1978), pp. 327-331.
Nagler, "Observations on a Reaction Between the Lethal Toxin of *Cl. welchii* (Type A) and Human Serum", British J. Exptl. Path., vol. 20, (1939), pp. 473-485.
McClung, et al., "A Medium for the Nagler Plate Reactions for the Identification of Certain Clostridia", J. Bacteriology, vol. 51 (1946), pp. 750-752.
McClung, et al., "The Egg Yolk Plate Reaction for the Presumptive Diagnosis of Clostridium Sporegenes and Certain Species of the Gagrene and Batulmum Groups", J. Bacteriology, vol. 53, pp. 139-147.
Kushner, "An Evaluation of the Egg-Yolk Reaction as a Test for Lecithinase Activity", J. Bacteriology, vol. 73, (1957), pp. 297-301.
Batzri et al., "Single Bilayer Liposomes Prepared Without Sonication", Biochim. Biophys. Acta, vol. 298 (1973), pp. 1015-1019.
Aarts et al., "Dynamics of Phospholipid Aggregation in Ethanol-Water Solutions", Chemistry and Physics of Lipids, vol. 19 (1977), pp. 267-274.
Difco Laboratories Technical Information, "Serological Reagents for Diagnosis of Syphilis", 1976.

*Primary Examiner*—Thomas G. Wiseman
*Attorney, Agent, or Firm*—Mallinckrodt & Mallinckrodt

[57] ABSTRACT

A uniform dispersion of a phospholipid in an aqueous based, salt containing solution may be obtained by dissolving the phospholipid in an alcohol chosen from the group consisting of methanol, ethanol, propanol, and isopropyl alcohol, and adding the phospholipid-alcohol solution to the aqueous based solution. The uniform dispersion will remain, even if the alcohol is evaporated or otherwise removed from the aqueous solution. If lecithin or certain other phospholipids useful in testing for the presence or activity of phospholipase C or A enzymes are uniformly dispersed in this manner, the resulting aqueous dispersion may be solidified by the addition of a hardening agent, such as agar, and the so-solidified dispersion used in an improved testing procedure for such enzymes. The enzymes will cause areas of hydrolysis to occur when placed in wells cut in the solidified dispersion, the size of these areas indicating the amount of enzyme present.

9 Claims, 3 Drawing Figures

4,140,579

METHOD OF TESTING FOR PHOSPHOLIPASES USING A COMPOSITION CONTAINING A UNIFORM DISPERSION OF A PHOSPHOLIPID

BACKGROUND OF THE INVENTION

1. Field

The invention is in the field of biochemical methods of testing for the presence of phospholipases, particularly phospholipase C, including methods for the preparation of aqueous based dispersions of phospholipids.

2. State of the Art

It is often desirable to test for the presence of phospholipases, particularly phospholipase C. Phospholipase C is an enzyme capable of reacting with and breaking down lecithin. This adverse reaction ultimately leads to cell breakdown and tissue destruction.

The presence of phospholipase C with Clostridium, Staphylococcus, or Pseudomonas bacteria indicates the pathogenic species of such bacteria, while absence of phospholipase C indicates the non-pathogenic species. Absence of phospholipase C with Bacillus bacteria indicates the pathogenic species of that bacteria.

Presently there are two methods of testing for the presence of or, if present, for activity of the phospholipase C enzyme. One method uses either purified lecithin or egg yolks (egg yolks contain lecithin) in a saline solution to which the material to be tested for the presence of phospholipase enzyme is added. The phospholipase enzyme splits the lecithin in the saline solution into an acid soluable phosphate. The amount of phosphate in the solution is then measured by usual means such as by a spectrophotometer, the amount of phosphate being an indication of the presence and activity of the phopholipase. Since this test measures phosphate, it is limited in its sensitivity to the sensitivity of the phosphate test.

Also, in order to obtain a suspension of lecithin in an aqueous based saline solution when using purified lecithin, the lecithin-saline solution must be sonicated (bombarded by sound waves) to break the lecithin down into micelles. The micelles then form a suspension in the solution. However, the micelles formed by sonication are not uniform, and, thus, the suspension in the saline solution is not uniform. This makes it extremely difficult to get consistant results. Further, because lecithin breaks down very rapidly at elevated temperatures, the purified lecithin cannot be sterilized. This means that a sterilized lecithin-saline solution cannot be obtained. Thus, when purified lecithin is used, the test cannot have clinical application in instances in which a sterile solution is necessary. It is also difficult to obtain the same results with phospholipase enzymes from different genera when using purified lecithin derived from different lecithin sources, e.g. purified lecithin derived from egg yolks or soybeans.

Egg yolks, when used, are difficult to handle because sterile precautions must be observed and shelf life of the egg yolks or egg yolk-saline solution is limited to only about a week. Further, the egg yolks give inconsistant results from test to test, and although presence of phospholipase enzyme may be determined, it is difficult to standardize the tests to obtain quantitative results.

The second test currently in use utilizes egg yolk in an agar medium. The material being tested for presence or activity of phospholipase enzyme is introduced into wells, i.e. depressions, formed in the agar. The phospholipase enzyme breaks down the lecithin in the agar. This breaking down or hydrolysis of the lecithin causes discoloration (darkening) of the agar medium. The amount and extent of hydrolysis extending from the well indicates directly the presence and activity of the phospholipase enzyme. The advantage of this test is that the phospholipase activity is measured directly, rather than indirectly as by measuring phosphate content in the test previously described, and is thus much more sensitive. The same disadvantage of egg yolk handling and test inconsistencies are present with this test using egg yolks as described in the previous test. In addition, the egg yolk-agar is non-specific, i.e. positive results can be obtained with enzymes other than phospholipase because of reaction of components of the egg yolk other than lecithin.

The agar test, although having advantages over the saline solution test, has not utilized purified lecithin because no method has yet been found to suspend the lecithin in the agar medium and maintain a uniform suspension during the time the medium is hardening. A uniform suspension is necessary for reproduceable results. The use of purified lecithin would be advantageous because of elimination of the other components of egg yolk, which can cause the positive reaction to occur without the phospholipase being present, and because a known uniform concentration of lecithin can be used from test to test.

SUMMARY OF THE INVENTION

According to the invention, a uniform dispersion of a phospholipid, such as lecithin, is obtained in an aqueous salt-containing solution, such as an agar basal medium, by dissolving the phospholipid in alcohol and then adding the phospholipid-alcohol solution to the aqueous solution. It has been found that, in this manner, a uniform dispersion of the phospholipid in the aqueous solution occurs and that a stable and uniform dispersion remains, even if the alcohol is evaporated or otherwise removed from the aqueous solution.

In the preparation of lecithin-agar plates for the testing for phospholipase enzymes, lecithin is dissolved in an alcohol such as ethanol. The lecithin-alcohol solution may be filter sterilized, and then added to an agar-basal medium solution which is allowed to harden in a petri dish. When hard, the medium is ready for use.

Wells are cut into the medium and the material to be tested is inserted into the wells. The presence of phospholipase C causes hydrolysis to occur in the lecithin in the agar medium, causing the medium to turn a dark color. The extent of the change in color indicates the amount of the enzyme present. The presence of phospholipase A causes hydrolysis of the lecithin to form a clear ring about the wells, again, the extent of the hydrolysis indicating the amount of enzyme present. Phospholipase D causes no reaction in the medium so cannot be detected.

THE DRAWINGS

Graphs indicative of the results obtained by use of the precedure presently contemplated as the best mode of carrying out the invention are shown in the accompanying drawings, in which:

FIG. 1 is a graph comparing results obtained using the phospholipase C test of the invention with those obtained using the conventional egg yolk-agar phospholipase C test;

FIG. 2, a graph showing the results obtained using the described phospholipase C test of the invention with different batches of test medium and type III phospholipase C enzyme; and FIG. 3, a graph showing the results obtained using the described phospholipase C test of the invention with different batches of test medium similar to those of FIG. 2, and type I phospholipase C enzyme.

DETAILED DESCRIPTION OF THE ILLUSTRATED EMBODIMENT

Figure 1:
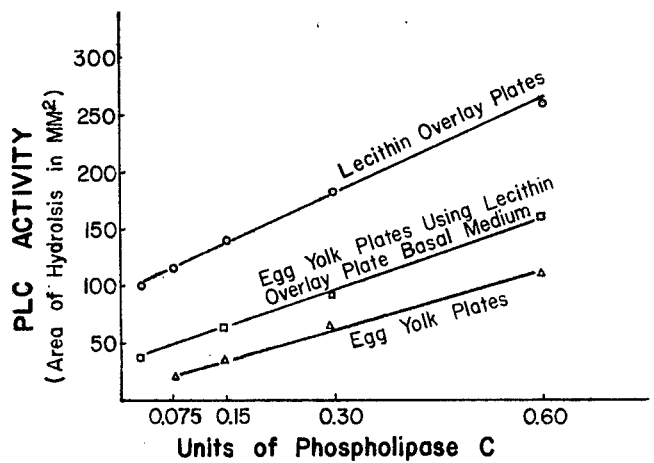

To perform a test for the presence of or for activity of phospholipase C or A enzymes according to the present invention, a uniform dispersion of lecithin in an appropriate test medium is prepared. The presently preferred test medium is a solid agar medium, so that test results can be determined directly by measurement of the area of hydrolysis. However, liquid media could also be used.

It has been found that a uniform dispersion of lecithin or other phospholipid in an aqueous salt-containing solution may be obtained by dissolving the phospholipid in an alcohol, preferably either methanol, ethanol, propanol, isopropyl alcohol, or mixtures thereof, and then adding the phospholipid-alcohol solution to the aqueous solution. The salt helps maintain the dispersion. Only a slight amount is needed. The uniform dispersion is maintained when the solution is hardened, such as by an agar hardening agent, to form a uniform dispersion in the agar. The alcohol may be evaporated or otherwise removed from the solution without affecting the dispersion.

It has also been found that the lecithin or other phospholipid may be very effectively sterilized (the alcohol does not sufficiently sterilize it), so that a completely sterile solution may be obtained, by filter sterilizing the phospholipid-alcohol solution and then adding that sterile solution to the aqueous solution which has been sterilized in any suitable manner.

The solution cannot be filter sterilized once the phospholipid is in the aqueous solution, because the phospholipid forms a suspension in the aqueous solution rather than a solution and would be filtered out along with the contaminants.

Normal membrane filters cannot be used to filter the phospholipid-alcohol solution, because the alcohol destroys the membranes. Therefore, a filter which is not affected by alcohol, such as an asbestos Seitz filter, must be used.

For use in testing for phospholipase C or A enzyme, lecithin is the preferred phospholipid. Other phospholipids that could be used are phosphatidyl ethanalamine, phosphatidyl serine, phosphatidyl inositol, and sphingomylin. These other phospholipids are expensive compared to lecithin, so their use is not presently economically practical.

Several agar plates were prepared for experimental purposes as described below. The preferred method of preparing the plates results in an overlay layer of the lecithin agar above a layer of a nutritive agar. For this reason, the preferred agar plates will be referred to as "lecithin overlay" plates. It should be realized, however, that various other forms of agar plates may be made according to the invention.

Lecithin overlay plates for use in testing for the presence or activity of phosphalipase C were prepared by placing 100 milliliters of 1.5% Ionagar available from Oxoid, Chicago, Illinois, with two percent (w/v) NaCl in a 500 ml sidearm flask containing a Teflon coated Magnetic stir bar and fitted with a Seitz Sterilizing Filter size G-9. The entire apparatus and contained solution was sterilized by autoclaving at 121° C. for 15 minutes. Immediately upon removal from the autoclave, 25 ml of saturated lecithin solution, equilibrated to 50° C., was filtered through the sterilizing filter into the hot medium, and the mixture was vigorously stirred under a slight vacuum until it had cooled to about 50° C. Ten ml portions of this mixture were added as overlay to 10 ml of precooled Beef Heart Infusion agar in a 100 mm plastic petri dish. Petri dishes containing the Beef Heart Infusion agar were precooled by placing them in a refrigerator at 5° C. for 20–30 minutes to speed solidification of the overlay when added. After adding the overlay, the plates were tempered at room temperature overnight and used the next day.

The saturated lecithin solution was prepared by washing soybean lecithin, Technical grade, available from Matheson. Coleman and Bell, Norwood, Ohio, three times in acetone, drying it in vacuuo, and then taking it up in a minimum volume of 95% ethanol. The lecithin-ethanol solution was filtered to remove particulate materials and vacuum distilled to ⅔ of the original volume to insure a saturated solution. A similar solution, but using egg yolk lecithin, was prepared by washing coagulated egg yolk, available from Difco Laboratories, Detroit, Michigan, with absolute alcohol and precipitating the soluble lecithin from the solution by pouring the alcoholic fraction into four volumes of cold acetone. The acetone precipitate was washed and redissolved in ethanol as described above for the soybean lecithin.

The lecithin is washed in acetone to remove the products of decomposition, such as fatty acids and oxidized acids, that naturally occur when lecithin is kept over a period of time. These products of decomposition are removed by the acetone, so that pure lecithin remains. The pure lecithin is white in color, while the products of decomposition turn the lecithin a yellow color. It has been found that three washings is generally sufficient to insure that the lecithin is pure; however, fewer washings may be sufficient where very little decomposition of the lecithin has taken place. The color of the lecithin serves as a good indication of its pureness.

It is important that the lecithin used be pure and that the lecithin-ethanol solution be saturated so that the concentration of lecithin in the medium is kept consistant from batch to batch merely by adding the same amount of the lecithin-ethanol solution to the same amount of basal medium. The consistency insures reproducible results. Of course, a known concentration could be obtained by measuring the amount of lecithin to be added to the ethanol and insuring that it is completely dissolved.

Beef Heart Infusion agar was prepared by adding 50 grams of Beef Heart for Infusion and 10 grams of Proteose Peptone No. 3 (both available from Difco Laboratories) to one liter of glass distilled water and allowing the mixture to infuse overnight at 4° C. The infusion was adjusted to pH 6.9 with KOH and boiled for 1 minute. After filtering through cheese cloth, Whatman No. 5 filter paper, and a Seitz Clarifying filter, Grade G-5, the pH was readjusted to 6.9. Agar, available from Difco Laboratories, was added to the filtered mixture to a final concentration of 1.5%. The mixture was sterilized at 121° C. for 15 minutes.

Phospholipase C type I (from Clostridum bacteria) and type III (from Bacillus bacteria), Phospholipase A (from bee venom) and Phospholipase D (from cabbage)

were obtained from Sigma, St. Louis, Missouri. Phospholipase C types I and III were diluted in 50% (v/v) aqueous glycerol solution. Phospholipases A and D were diluted with sterile distilled water.

Wells of 5 mm diameter were cut into the lecithin overlay plates and 10 microliters of diluted enzyme were placed in individual wells. The plates were incubated at 37° C. for 11 hours. To prevent drying due to evaporation, plates were placed in a sealed vessel prior to incubation. Measurements of diffusion-reaction zones (zones of hydrolysis) were determined directly with a 7X Polaron hand lens fitted with a measuring micrometer.

For comparison test purposes, egg yolk plates were prepared in the customary manner as described by McClung and Toabe in an article entitled "A Medium for the Nagler Plate Reaction for Identification of Certain Clostridium" published in the Journal of Bacteriology, 1941, Vol, 51, pages 750–752. Basically, these plates are made by adding a saline, egg yolk solution to a 2% agar solution which has 2% NaCl added and some other salts added. The tests using the egg yolk plates were conducted in the same manner and under the same conditions as those utilizing the lecithin overlay plates described above.

The results of the tests using phospholipase C Type III are shown graphically in FIG. 1 and indicate a much greater sensitivity (a much larger area of measurable hydrolysis) when using the lecithin overlay plates than when using the standard egg yolk plates. In order to determine the effect of the slightly different basal medium used with the lecithin overlay plates and the standard egg yolk plates, a test was made using the same basal medium as with the lecithin overlay plates, but, rather than using the purified lecithin dissolved in ethanol, a saline, egg yolk solution was used. This showed somewhat larger areas of hydrolysis than the normal egg yolk plates, as illustrated, but was still far from the increased area of hydrolysis obtained with the lecithin overlay plates.

The conventional egg yolk plate required a minimum of 0.0125 units of phospholipase C enzyme before presence of the enzyme could be detected. With the lecithin overlay plates, as little as 0.005 units of phospholipase C enzyme were easily detected and extrapolation of the experimental results indicated that even smaller amounts of the enzyme could have been detected.

The position of the line representing the area of hydrolysis when the conventional egg yolk plates are used will vary from egg yolk to egg yolk because concentration of the lecithin and concentration of various other constituents in the egg yolk, some of which inhibit the reaction with the lecithin, vary from egg yolk to egg yolk. The area of hydrolysis obtained for equivalent units of phospholipase enzyme using egg yolk plates will never reach the area of hydrolysis using lecithin overlay plates, because of the presence of reaction inhibiting components in the egg yolk. The variation itself, however, is the major problem encountered using egg yolk plates. With the lecithin overlay plates, as long as the lecithin used is substantially pure so that consistent concentrations are used, the position of the line will be constant and reproducible.

Figure 2:
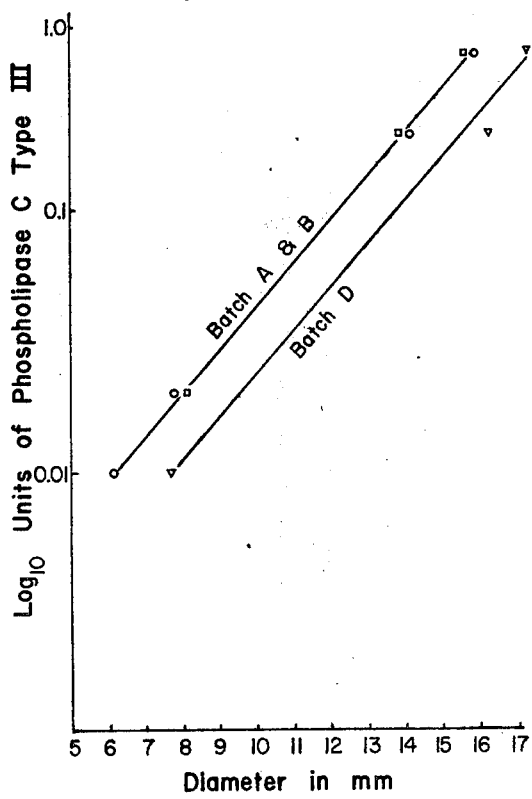

To determine whether or not the results using the lecithin overlay plates were reproducible (reproducibility is a major problem when using different batches of egg yolk medium), standard enzyme curves for phospholipase types I and III were generated using three different batches of lecithin. Batch A was acetone-washed, soybean-derived lecithin as described. Batch B was egg-yolk-derived lecithin prepared in the same manner as described. Batch D was similar to batch A, except batch D was washed only once with acetone rather than three times. The results of assays using type III phospholipase C enzyme, see FIG. 2, indicate that when egg yolk and soybean lecithins are prepared in an identical manner, the rates of hydrolysis will be very similar. When less extensively washed soybean lecithin was used in the medium for types I and III phospholipase C enzymes, the area of hydrolysis was greater by approximately 10% than the area of hydrolysis for an equivalent amount of enzyme assayed in the more extensively washed lecithin. The slope of the line generated with the less extensively washed lecithin, however, was identical to the slopes generated by assays using other batches of lecithin.

The difference in positions of the lines generated using the extensively washed lecithin as against the less extensively washed lecithin is probably due to the presence of products of decomposition in the latter, which produced a lesser concentration of lecithin in the test medium.

The lecithin that had been washed three times, and was therefore substantially pure, showed consistent results. This indicated that reproducible results are obtainable using pure lecithin.

Regardless of the positions of the lines, the fact that the slopes are equal indicates that the same amount of change in area of hydrolysis represents the same amount of change in units of phospholipase enzyme present. This, in itself, is a significant advantage over the egg yolk plate test.

Figure 3:
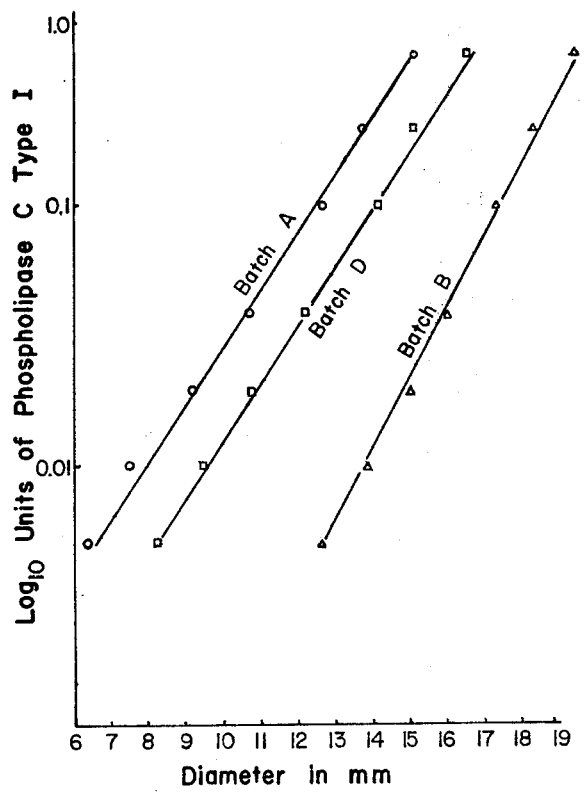

Type I phospholipase C enzyme produced similar test results to those obtained with the type III when the soybean-derived lecithin medium was used, but produced greater areas of hydrolysis in the medium prepared with the egg-yolk-derived lecithin. The test results using type I phospholipase C enzyme are shown graphically in FIG. 3.

The difference in results obtained when testing type I phospholipase C enzyme, using medium made with soybean-derived lecithin, is probably due to the difference in the ionic requirements of the phospholipase C types I and III. The egg-yolk-derived lecithin probably contains a higher concentration of calcium ion than does the soybean-derived lecithin. Calcium ion is required by the type I enzyme, but not by the type III enzyme. With the addition of Ca++ to the soybean-derived lecithin medium, the type I enzyme showed increased areas of hydrolysis.

One unit of phospholipase C enzyme, as used in the figures of the drawings, is defined as the amount of enzyme that will liberate 1 micromole of acid soluble phosphorus, permanent at 37° C. Phospholipase C is also known by its more technical name phosphadityl-choline cholinephosphohydrolase and is identified by the Enzyme council number 3.2.4.3.

Conventional egg yolk medium used in egg yolk plates produces dark areas of hydrolysis with phosphoslipase A enzymes as well as with phospholipase C enzymes. With the lecithin overlay plates of the present invention, phospholipase A enzymes produce clear areas of hydrolysis. There is thus a positive differentiation between the phospholipase C and the phospholipase A enzymes when using the testing method of the present invention.

It should be noted that phospholipase D enzyme is not detected by either the conventional test or the test of the invention.

The phospholipase testing described is one aspect of and one use of the present invention, which, broadly speaking, provides a method of obtaining a uniform suspension of a phospholipid in an aqueous, salt-containing solution. Since it appears that the phospholipids form uniform micelles in such an aqueous solution, the aspect of the invention concerned with the production of such a uniform suspension can be used whenever and wherever it is desired to produce uniform micelles. Such micelles may then be separated from the solution in known manner and used as found appropriate.

Whereas this invention is here described with specific reference to an embodiment thereof presently contemplated as the best mode of carrying out such invention in actual practice, it is to be understood that various changes may be made in adapting the invention to different embodiments without departing from the broader inventive concepts disclosed herein and comprehended by the claims that follow.

I claim:

1. A method of testing for the presence of or for activity of phospholipase C or A, comprising the steps of preparing an aqueous, salt-containing, basal medium; dissolving a purified phospholipid chosen from the group consisting of purified lecithin, phosphohydyl ethanalamine, phosphohydyl serine, phosphatidyl inositol, and sphingomylin, in an amount of an alcohol sufficient to form a solution wherein the alcohol is chosen from the group consisting of methanol, ethanol, propanol or isopropyl alcohol; adding the phospholipid-alcohol solution to the aqueous basal medium to form a dispersion; adding a hardening agent to the dispersion; allowing the dispersion to harden forming a substrate medium; cutting a well in the hardened substrate medium; placing the sample to be tested for presence or activity of phospholipase C or A in the well; incubating the sample in the well under conditions suitable for said phospholipase reaction to occur; and observing the existence and extent of hydrolysis of the substrate medium surrounding the well.

2. A method according to claim 1, wherein the hardening agent is agar.

3. A method according to claim 2, including the steps of sterilizing the basal medium before addition of the phospholipid-alcohol solution; and sterilizing the phospholipid-alcohol solution prior to adding it to the aqueous basal medium, the said sterilization being accomplished by passing such phospholipid-alcohol solution through a filter having filter openings small enough to block passage of contaminants while passing the phospholipid-alcohol solution.

4. A method according to claim 2, including the step of providing a hardened agar basal medium upon which the substrate medium is hardened to form an upper layer.

5. A method according to claim 1, including the additional step of removing at least some of the alcohol from the dispersion before the step of adding a hardening agent to the dispersion.

6. A method according to claim 5, wherein all of the alcohol is removed from the dispersion before the step of adding a hardening agent to the dispersion.

7. A product for use in testing for the presence of, or for activity of, phospholipase C or A comprising a uniform distribution of purified lecithin in a hardened, aqueous, salt-containing medium, said product made by adding an alcohol-lecithin solution to an aqueous salt-containing solution to form a dispersion, adding a hardening agent to the dispersion, and then allowing the dispersion to harden, and wherein said product contains a well for receiving a sample of material to be tested for the presence or activity of phospholipase C or A.

8. A product according to claim 7, wherein the uniform distribution of purified lecithin in a hardened, aqueous, salt-containing medium, is hardened as a layer over a layer of hardened, non-lecithin containing medium.

9. A product according to claim 7, wherein the hardening agent is agar.

* * * * *